(12) United States Patent
Campagna et al.

(10) Patent No.: US 8,510,882 B2
(45) Date of Patent: Aug. 20, 2013

(54) METHOD AND APPARATUS FOR ANATOMICAL POSITIONING ON A PATIENT CARE PLATFORM

(76) Inventors: Michael Campagna, Oak Park, IL (US); Jonathan S. Citow, Glencoe, IL (US)

( * ) Notice: Subject to any disclaimer, the term of this patent is extended or adjusted under 35 U.S.C. 154(b) by 0 days.

(21) Appl. No.: 12/464,456

(22) Filed: May 12, 2009

(65) Prior Publication Data
US 2010/0071128 A1     Mar. 25, 2010

Related U.S. Application Data

(60) Provisional application No. 61/098,757, filed on Sep. 20, 2008.

(51) Int. Cl.
*A61G 13/10*     (2006.01)
*A61G 13/12*     (2006.01)

(52) U.S. Cl.
USPC ................ 5/621; 5/623; 5/646; 128/878

(58) Field of Classification Search
USPC ..... 5/621, 623, 624, 622, 646, 647; 128/877, 128/878
See application file for complete search history.

(56) References Cited

U.S. PATENT DOCUMENTS

| 5,056,535 A * | 10/1991 | Bonnell ................. 128/882 |
| 5,802,641 A * | 9/1998 | Van Steenburg ............ 5/648 |
| 6,108,841 A * | 8/2000 | Cameron et al. ............ 5/648 |
| 2002/0157186 A1* | 10/2002 | VanSteenburg et al. ...... 5/621 |
| 2004/0123389 A1* | 7/2004 | Boucher et al. ............ 5/623 |
| 2006/0242765 A1* | 11/2006 | Skripps et al. ............. 5/621 |

* cited by examiner

*Primary Examiner* — Michael Trettel
(74) *Attorney, Agent, or Firm* — Ariel S. Bentolila; Bay Area IP Group, LLC

(57) ABSTRACT

An apparatus for mounting an anatomical positioner on a patient care platform includes a clamping mechanism for allowing an operator to quickly and securely join the apparatus to the patient care platform. Guide rails are joined to the clamping mechanism. The guide rails extend away from the patient care platform. Slides slidably join to the guide rails to allow the operator to position the anatomical positioner to impart a force on a patient on the patient care platform. The slides include brakes for at least stopping movement in a direction away from the patient care platform, and brake releases for releasing the brakes. Supports join to the slides for supporting the anatomical positioner. The supports have restraints for allowing the operator to quickly secure and adjust the anatomical positioner, whereby the anatomical positioner is positioned by the operator to impart the force on the patient and locked in place.

23 Claims, 1 Drawing Sheet

METHOD AND APPARATUS FOR ANATOMICAL POSITIONING ON A PATIENT CARE PLATFORM

CROSS-REFERENCE TO RELATED APPLICATIONS

The present Utility patent application claims priority benefit of the U.S. provisional application for patent Ser. No. 61/098,757 filed on 20 Sep. 2008 under 35 U.S.C. 119(e). The contents of this related provisional application are incorporated herein by reference for all purposes.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

FIELD OF THE INVENTION

The present invention relates generally to medical equipment. More particularly, the invention relates to a table mount for use with a shoulder press that positions patient's shoulders during medical procedures.

BACKGROUND OF THE INVENTION

Best practices demand correct visualization of the vertebrae intraoperatively for all surgical approaches involving the cervical spine. The Citow Cervical Visualizer (CCV) has proven to be a safe and effective means by which a spine surgeon can correctly ascertain that surgery is being performed at the correct level, thereby significantly diminishing the possibility of wrong site surgery in the cervical vertebrae. The CCV is a handheld radiolucent shoulder positioning device, or shoulder press, designed to facilitate and optimize the visualization of the cervical vertebrae during surgical approaches by moving and holding the shoulders out of the way in order to visualize an additional two to three vertebrae. Accomplishing this task via the usage of a pair of radiolucent carbon fiber pusher tubes that terminate in matched radiolucent arches, the CCV utilizes an adjustable horizontal crossbar tipped with ergonomic handgrips to transmit the necessary 24 to 37 pounds of motive force upon the patient's shoulders (i.e., the Acromion Clavicular joint) facilitating the transient movement of these structures and thereby allowing optimized visualization of the cervical vertebrae under X-Ray. The utilization of the CCV in this modality is effected by a live operator positioned at the head of the surgical table delivering this motive force thru handheld positioning and manipulation. Thus, the live operator is exposed to radiation from the X-Rays, which is an undesirable consequence of using the CCV. Furthermore, the CCV is often used in a complex surgical environment comprising a multitude of leads, lines and monitoring equipment around which the operator must maneuver, which may be a very difficult task.

In view of the foregoing, there is a need for improved techniques for providing means for using a shoulder press such as the CCV on a patient without a live operator that may be easily employed in a complex surgical environment.

BRIEF DESCRIPTION OF THE DRAWINGS

The present invention is illustrated by way of example, and not by way of limitation, in the figures of the accompanying drawings and in which like reference numerals refer to similar elements and in which.

Figure 1:
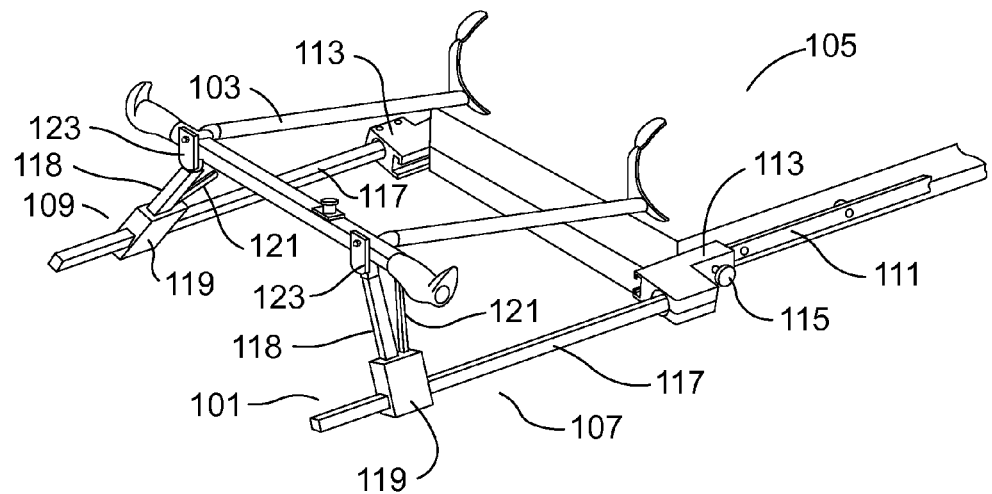
FIG. 1 illustrates an exemplary universal table mount for a shoulder press in use on a surgical table, in accordance with an embodiment of the present invention.

Unless otherwise indicated illustrations in the figures are not necessarily drawn to scale.

DETAILED DESCRIPTION OF THE PREFERRED EMBODIMENTS

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

The present invention will now be described in detail with reference to embodiments thereof as illustrated in the accompanying drawings.

Preferred embodiments of the present invention provide a table attached device, or universal table mount, for a shoulder press that provides a firm and stable, horizontal cradled platform upon which the shoulder press can travel and lock in such a way as to effectively and consistently replicate the action and application of sustained force for the duration of an X-Ray, which would otherwise be delivered by a live operator. By providing a generally consistent and reliable platform, the table mount allows for the reliable and correct positioning and quick release of the shoulder press without the necessity or presence of a live operator during the actual patient X-Ray, thereby generally eliminating the possibility of exposure to radiation for all personnel. Without a table mount according to preferred embodiments, the handheld nature of the shoulder press device offers no such protection and precludes the use of the shoulder press device in environments where a C-ARM (i.e., Intraoperative Flouroscope) is utilized due to harmful exposure levels. Additionally, by providing a stable platform for the shoulder press throughout the entire duration of a surgical procedure, the table mount allows for one time set-up and continuous positioning of the shoulder press in immediate proximity to the usage site, thereby generally eliminating the complicated procedure of maneuvering and positioning the shoulder press in the ubiquitous environment of leads, lines, anesthesia and monitoring equipment, as well as greatly simplifying the usage of the shoulder press without disturbing these sensitive arrays. However, alternate usages for preferred embodiments of the present invention may be conceived such as, but not limited to, usage in an X-Ray room, usage by paramedics, usage in the trauma specialty for diagnosis, usage by orthopedic surgeons as a surgical positioner for patient extremities during revision hip arthroplasty, etc. Further alternate usages for preferred embodiments of the present invention may also be conceived such as, but not limited to, usage in various surgical, diagnostic and imaging procedures as an anatomical positioner for applications throughout the entire human anatomy relating to all aspects of patient care and specialties. Yet other alternative usages for preferred embodiments of the present invention may also be conceived such as, but not limited to, usage relating to all surgical specialties as a platform for the positioning and manipulation of tools, equipment, and necessities relating to all aspects of patient care, including, but not be limited to, surgical, diagnostic and imaging of patients. It is further contemplated that alternate usages for preferred embodiments of the present invention may also be conceived such as, but not limited to, usages relating to all aspects of veterinary care.

FIG. 1 illustrates an exemplary universal table mount 101 for a shoulder press 103 in use on a surgical table 105, in accordance with an embodiment of the present invention. In the present embodiment, table mount 101 is comprised of two distinct yet mirror imaged sections, a dedicated right section 107 and a dedicated left section 109. Alternate embodiments may be implemented in which the left and right sections of the mount are connected. In the present embodiment, right section 107 and left section 109 clamp onto surgical table 105, which is equipped with industry standard accessory side rails 111 provided by table manufacturers for the use of the surgical staff in mounting various necessary equipment to surgical table 105 for use during surgery. Accessory side rails 111 may use American standard or metric measurements, and universal table mounts according to preferred embodiments of the present invention may be available in distinct clamping sizes to accommodate these industry standards. Right section 107 and left section 109 of table mount 101 slide easily onto accessory side rails 111, and an attachment mechanism 113 mates onto accessory side rails 111 and may be fixed in place by tightening a simple twist dial 115 secured with a simple twist dial 115. Guide rails 117 extend from attachment mechanisms 113 onto which upward supports 118 are slidably attached with slides 119. Attachment mechanisms 113 are preferably made of aluminum; however, the attachment mechanisms in alternate embodiments may be made of different materials such as, but not limited to, different metals or plastic. Guide rails 117 and upward supports 118 are preferably one-inch square aluminum bars. However, those skilled in the art, in light of the present teachings, will readily recognize that the mount rails and upward supports in alternate embodiments may be made in different shapes and sizes and be made of various different materials such as, but not limited to, different metals or plastic. Furthermore, slides 119 are preferably made of plastic; however, alternate materials such as, but not limited to, various metals may also be used. In the present embodiment, slides 119 comprise handbrakes 121 that enable upward supports 118 to be locked into place on guide rails 117.

In typical use of the present embodiment, after mounting table mount 101 to accessory side rails 111, placement of shoulder press 103 within a shoulder press cradle is quick and easy, and shoulder press 103 is secured within the shoulder press cradle with adjustable/pivoting L-Shaped restraints 123 provided to accommodate this function. After positioning and adjusting shoulder press 103 to the proper width to effectively migrate the shoulders distally within table mount 101, an operator may apply the 24 to 37 pounds of motive force upon the Acromion-Clavicular joint with shoulder press 103 by squeezing handbrakes 121 and pushing upward supports 118 or shoulder press 103 toward the patient on surgical table 105. The application of motive force by the operator along with the hand actuation of handbrakes 121 advances the position of shoulder press 103. When shoulder press 103 is correctly positioned, the operator releases handbrakes 121 to lock sliders 119 and therefore shoulder press 103 in place. The operator may swiftly and easily unlock and move shoulder press 103 away from the patient by squeezing handbrakes 121 and pulling back. Some embodiments may also comprise a quick release mechanism for the handbrakes so that the shoulder press may be immediately moved away from the patient in case of an emergency.

In alternate embodiments, the travel of the upward supports and the shoulder press within the shoulder press cradle along the guide rails is unidirectional toward the patient. In these embodiments the upward supports are able to move freely toward the patient and are prevented from moving away from the patient through the incorporation of an internal friction braking system. The actuation of a brake release allows for a reversal of travel away from the patient by releasing the internal friction braking system. The friction brake resists all backward motion due to tilting and comprises a hand control that reorients the tilt by finger tapping in order to enable backward movement. The friction brake preferably uses a large trigger somewhat akin to a bicycle handbrake lever. However, a bicycle brake uses a caliper style set of rubber pads whereas this friction brake uses no calipers, discs or pads and instead utilizes the slight offset of a channel and the guide rail of the table mount to halt backward motion unless the internal offset is lessened through application of the trigger/brake release. Other alternative embodiments may employ differing means for halting the backward motion. These other alternative means will also have at least one hand control means for enabling backward movement.

Figure 2:
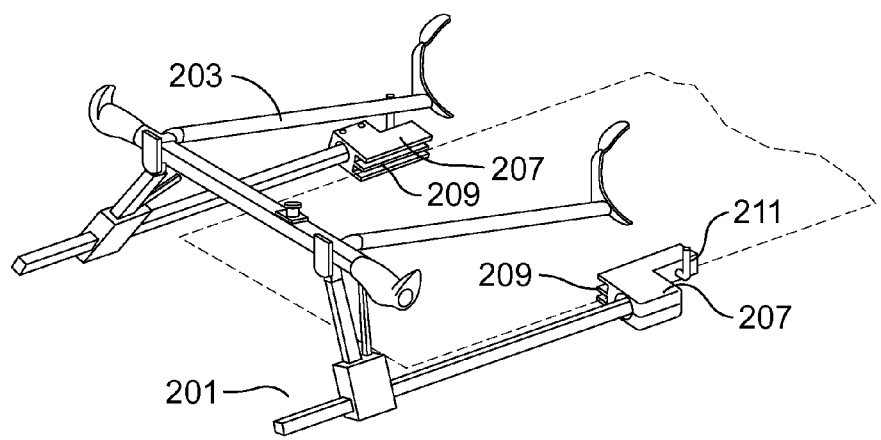
FIG. 2 illustrates an exemplary table mount for a shoulder press for use on patient surfaces without side rails, in accordance with an embodiment of the present invention.

FIG. 2 illustrates an exemplary mount 201 for a shoulder press 203 for use on patient surfaces without side rails, in accordance with an embodiment of the present invention. In the present embodiment, mount 201 comprises variable clamps 207 rather than attachment mechanisms for sliding onto an accessory side rail. Variable clamps 207 slide over the edges of a patient surface and are held in place by actuating plates 209 that squeeze the edges of the patient surface when clamp locks 211 are employed. In other alternative embodiments clamps may be locked into position by any number of devices such as, but not limited to, levers, dials, knobs, etc. that are deemed appropriate to the patient anatomy the alternate embodiments address. This enables mount 201 to be attached to surfaces other than operating room surgical tables with side rails for example, without limitation, other types of patient beds and tables, paramedic long boards, imaging tables, exam tables, etc., any other patient care surfaces unrestricted to unrestricted to horizontal positions, and whatever variable geometry offered by the patient care surface, whether fixed or movable during usage Paramedics often carry patients on long boards, and when a patient has a suspected subluxation injury (i.e., broken neck), they are brought to the emergency room (ER) on such a long board and typically remain on this long board throughout the ER experience. In typical use of the present embodiment, shoulder press 203 may be attached to a long board with mount 201 to quickly assist in correct visualization of the cervical spine of the patient to determine if there is an injury.

Having fully described at least one embodiment of the present invention, other equivalent or alternative methods of providing a table mount for a shoulder press or anatomical positioner according to the present invention will be apparent to those skilled in the art. The invention has been described above by way of illustration, and the specific embodiments disclosed are not intended to limit the invention to the particular forms disclosed. For example, the particular implementation of the table mount may vary depending upon the particular type of shoulder press used. The table mounts described in the foregoing were directed to implementations for use with the CCV; however, similar techniques are to implement table mounts for use with various different shoulder presses, anatomical positioners, equipment positioners, etc. Implementations of the present invention implemented for use with shoulder presses other than the CCV are contemplated as within the scope of the present invention. The invention is thus to cover all modifications, equivalents, and alternatives falling within the spirit and scope of the following claims.

What is claimed is:

1. An apparatus comprising:
    means for securely joining to a patient care platform;
    means for extending away from an end of the patient care platform only in a plane defined by lengthwise sides of the patient care platform, said extending means being joined to said joining means;
    means for moving along a length of said extending means;
    means for stopping movement of said moving means in a direction away from a patient laying on the patient care platform and for selectively enabling free movement of said moving means; and
    means for joining a Citow Cervical Visualizer type shoulder press with said moving means, the shoulder press being positioned by movement of said moving means along said extending means and held in place by said stopping means for selectively holding the shoulder press pressured onto the patient's shoulders with the shoulders resting on the patient care platform.

2. The apparatus as recited in claim 1, in which movement towards the patient is not inhibited by said stopping means.

3. An apparatus comprising:
    at least one clamping mechanism for quickly and securely joining the apparatus to lengthwise sides of a patient care platform;
    at least one guide rail being rigidly joined to said at least one clamping mechanism for extending away from an end of the patient care platform only in a plane defined by the lengthwise sides of the patient care platform;
    at least one slide being slidably joined to said at least one guide rail to enable positioning of said slides along at least portions of said guide rails;
    at least one handbrake mechanism being joined to said at least one slide for stopping movement of said at least one slide in a direction away from a patient laying on the patient care platform and for selectively enabling free movement of said slides; and
    at least one support being joined to said at least one slide, said at least one support being operable for supporting at least a portion of a Citow Cervical Visualizer type shoulder press, said at least one support comprising an upward support member and a restraint forming a portion of cradle for the shoulder press, said upward support member being configured to form an acute angle relative to a portion of the plane that includes the patient care platform when said apparatus is in actual and normal use, said cradle portion being operable to position the corresponding shoulder press portion by movement of said at least one slide along said at least one guide rail and held in place by said at least one handbrake mechanism to thereby be operable for selectively holding the shoulder press pressured onto the patient's shoulders with the shoulders resting on the patient care platform when said apparatus is in actual and normal use.

4. The apparatus as recited in claim 3, in which said restraints are pivotal.

5. The apparatus as recited in claim 3, in which said handbrake mechanisms comprise levers for operation.

6. The apparatus as recited in claim 3, in which said at least one guide rail is joined to said at least one clamping mechanism such that it has a separation distance greater than a width of the patient care platform.

7. The apparatus as recited in claim 3, in which said at least one clamping mechanism join to the accessory side rails of the patient care platform with a twist dial.

8. The apparatus as recited in claim 3, in which said at least one clamping mechanism clamp to surfaces of the patient care platform.

9. The apparatus as recited in claim 8, in which said at least one clamping mechanism clamp to surfaces of the patient care platform with an actuating plate.

10. The apparatus as recited in claim 3, in which said handbrake mechanisms incorporate a braking mechanism that is configured to enable an operator to move the slide in a direction towards the patient on the patient care platform and selectively control movement of said slide in a direction away from the patient.

11. The apparatus as recited in claim 3, in which said handbrake mechanisms are configured to be operable as quick releases that quickly release enabling an operator to promptly move the shoulder press away from the patient in an emergency situation.

12. The apparatus as recited in claim 3, in which said upward support members comprise a height higher than a shoulder area of a patient laying on the patient care platform to impart a downward force component onto the patient's shoulder area during use.

13. An apparatus comprising:
    a left assembly comprising:
    a left clamping mechanism for securely joining with a left side of the patient care platform;
    a left guide rail being rigidly joined with said left clamping mechanism for extending away from an end of the patient care platform only in a plane defined by the lengthwise sides of the patient care platform, said left guide rail being joined to said left clamping mechanism to have a separation distance away from the left side in the plane;
    a left slide slidably joined with said left guide rail, said left slide being operable to slide along at least a portion of said left guide rail;
    a left handbrake mechanism being joined to said left slide for stopping movement of said left slide in a direction away from a patient laying on the patient care platform and for selectively enabling free movement of said left slide; and a left support being joined to said left slide, said left support being operable for supporting a left side of a Citow Cervical Visualizer type shoulder press, said left support comprising a left upward support member and a left restraint forming a left side of a cradle for the left side of the shoulder press, said left upward support member being positioned at an acute angle relative to a portion of the plane to the right of said left guide rail, said left side of said cradle being operable to position the left side of the shoulder press by movement of said left slide along said left guide rail and to hold in place by said left handbrake mechanism to thereby enable selectively holding the shoulder press pressured onto the patient's left shoulder with the left shoulder resting on the patient care platform when said apparatus is in actual and normal use; and a right assembly comprising:

a right clamping mechanism for securely joining with a right side of the patient care platform;

a right guide rail being rigidly joined with said right clamping mechanism for extending away from the end of the patient care platform only in the plane, said right guide rail being joined to said right clamping mechanisms to have a separation distance away from the right side in the plane;

a right slide slidably joined to said right guide rail, said right slide being operable to slide along at least a portion of said right guide rail;

a right handbrake mechanism being joined to said right slide for stopping movement of said right slide in a direction away from the patient laying on the patient care platform and for selectively enabling free movement of said right slide; and a right support being joined to said right slide, said right support being operable for supporting a right side of a Citow Cervical Visualizer type shoulder press, said right support comprising a right upward support member and a right restraint forming a right side of the cradle for the right side of the shoulder press, said right upward support member being positioned at an acute angle relative to a portion of the plane to the left of said right guide rail, said right side of said cradle being operable to position the right side of the shoulder press by movement of said right slide along said right guide rail and to hold in place by said right handbrake mechanism to thereby enable selectively holding the shoulder press pressured onto the patient's right shoulder with the right shoulder resting on the patient care platform when said apparatus is in actual and normal use.

14. The apparatus as recited in claim 13, in which said left restraint and said right restraint are configured to be pivotal.

15. The apparatus as recited in claim 13, in which said left handbrake mechanism and said right handbrake mechanism each comprise a hand-operated lever.

16. The apparatus as recited in claim 13, in which said left clamping mechanism and said right clamping mechanism each clamp to an accessory side rail of the patient care platform.

17. The apparatus as recited in claim 16, in which said left clamping mechanism and said right clamping mechanism secure to the accessory side rails of the patient care platform with a twist dial.

18. The apparatus as recited in claim 13, in which said left clamping mechanism and said right clamping mechanism each clamp to a surface of the patient care platform.

19. The apparatus as recited in claim 18, in which said left clamping mechanism and said right clamping mechanism each clamp to the surface of the patient care platform with an actuating plate.

20. The apparatus as recited in claim 13, in which said left handbrake mechanism and said right handbrake mechanism each incorporate a braking mechanism that is configured to enable an operator to move the shoulder press onto the shoulders of a patient laying on the patient care platform and selectively control movement of the shoulder press in a direction away from the patient.

21. The apparatus as recited in claim 13, in which said left handbrake mechanism and said right handbrake mechanism are configured as quick releases that quickly release enabling an operator to rapidly move the shoulder press away from the patient in an emergency medical intervention.

22. The apparatus as recited in claim 13, said acute angles lie in an intersecting plane that is parallel to a face of the end of the patient care platform.

23. The apparatus as recited in claim 13, in which said left and right upward support comprise a height higher than a shoulder area of an average sized patient laying on the patient care platform to enable the shoulder press to impart a downward force component onto the shoulder area during use.

* * * * *